United States Patent
Bar-Tal et al.

(10) Patent No.: US 10,820,887 B2
(45) Date of Patent: Nov. 3, 2020

(54) INFLATABLE BALLOONS FOR A FOLDABLE APPARATUS

(71) Applicant: Biosense Webster (Israel) Ltd., Yokneam (IL)

(72) Inventors: Meir Bar-Tal, Haifa (IL); Dudu Haimovich, Ramat Yishai (IL); Roee Haimovich, Nesher (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 857 days.

(21) Appl. No.: 15/133,725

(22) Filed: Apr. 20, 2016

(65) Prior Publication Data

US 2017/0303896 A1    Oct. 26, 2017

(51) Int. Cl.
| | |
|---|---|
| A61B 8/00 | (2006.01) |
| G01S 15/89 | (2006.01) |
| A61B 8/08 | (2006.01) |
| A61B 8/12 | (2006.01) |
| A61M 25/10 | (2013.01) |

(52) U.S. Cl.
CPC ............ *A61B 8/445* (2013.01); *A61B 8/0883* (2013.01); *A61B 8/12* (2013.01); *A61B 8/4477* (2013.01); *A61B 8/4483* (2013.01); *A61B 8/4488* (2013.01); *G01S 15/8925* (2013.01); *A61M 2025/1015* (2013.01)

(58) Field of Classification Search
CPC ...... G01N 25/18; H01L 23/34; H05K 7/2039; A61B 8/445; A61B 8/4488; A61B 8/4483; A61B 8/0883; A61B 8/4477; A61B 8/12; G01S 15/8925; G01S 15/8934; A61M 2025/1015
See application file for complete search history.

(56) References Cited

U.S. PATENT DOCUMENTS

| | | | |
|---|---|---|---|
| 4,841,977 A * | 6/1989 | Griffith | A61B 8/12 29/25.35 |
| 5,342,307 A | 8/1994 | Euteneuer et al. | |
| 7,544,166 B2 * | 6/2009 | Yuan | A61B 8/12 600/437 |
| 8,894,614 B2 | 11/2014 | Muni et al. | |
| 2004/0242999 A1 | 12/2004 | Vitek et al. | |
| 2005/0215895 A1 * | 9/2005 | Popp | A61B 6/466 600/437 |
| 2006/0276711 A1 | 12/2006 | Yuan et al. | |
| 2007/0066902 A1 * | 3/2007 | Wilser | A61B 8/12 600/459 |
| 2007/0239011 A1 | 10/2007 | Lau et al. | |

(Continued)

OTHER PUBLICATIONS

Extended European Search report for corresponding European application No. 17167004.5, dated Oct. 17, 2017.

(Continued)

*Primary Examiner* — Carolyn A Pehlke
(74) *Attorney, Agent, or Firm* — Notaro, Michalos & Zaccaria P.C.

(57) ABSTRACT

Described embodiments include an apparatus that includes a plurality of flaps configured to fold over each other in a folded configuration. Each one of the flaps includes one or more ultrasound transducer elements. One or more balloons are coupled to the flaps, the balloons being configured to, upon being inflated, unfold the flaps from the folded configuration. Other embodiments are also described.

17 Claims, 4 Drawing Sheets

(56) References Cited

U.S. PATENT DOCUMENTS

| | | | |
|---|---|---|---|
| 2008/0091141 A1* | 4/2008 | Qureshi | A61M 25/104 604/96.01 |
| 2010/0004506 A1* | 1/2010 | Saadat | A61B 1/0008 600/109 |
| 2012/0004577 A1* | 1/2012 | Saadat | A61B 1/0008 600/587 |
| 2014/0180034 A1* | 6/2014 | Hoseit | A61B 5/6847 600/301 |
| 2015/0112188 A1* | 4/2015 | Stigall | A61B 17/064 600/424 |
| 2015/0165241 A1* | 6/2015 | Burdette | A61B 8/12 601/3 |

OTHER PUBLICATIONS

Israeli office action for corresponding application No. IL 251259, dated May 27, 2020.

\* cited by examiner

INFLATABLE BALLOONS FOR A FOLDABLE APPARATUS

FIELD OF THE INVENTION

The present invention relates generally to the field of medical devices, and specifically to devices for intra body use, such as intra cardiac use.

BACKGROUND

In some intra cardiac echography (ICE) applications, an ultrasound transducer is deployed, via a catheter, within the heart of a subject, and is used to acquire ultrasound images of the intra cardiac space.

U.S. Pat. No. 5,342,307, whose disclosure is incorporated herein by reference, describes a balloon of an angioplasty balloon catheter that is prepared for insertion through a patient's cardiovascular system by a series of steps to create three or more folded wings or flaps. The wings are wrapped circumferentially to provide a minimized outer diameter when the balloon is in its deflated state.

SUMMARY OF THE INVENTION

There is provided, in accordance with some embodiments of the present invention, apparatus including a plurality of flaps configured to fold over each other in a folded configuration, each one of the flaps including one or more ultrasound transducer elements. The apparatus further includes one or more balloons coupled to the flaps, the balloons being configured to, upon being inflated, unfold the flaps from the folded configuration.

In some embodiments, the balloons are configured to, upon being inflated, unfold the flaps from the folded configuration into a flat configuration.

In some embodiments, a respective subset of the balloons is coupled to each pair of adjacent ones of the flaps.

In some embodiments, the apparatus further includes one or more hinges that couple adjacent ones of the flaps to one another.

In some embodiments, the plurality of flaps are configured to fit inside a catheter while in the folded configuration.

In some embodiments, the flaps include at least three flaps.

In some embodiments, at least one of the balloons includes a plurality of compartments that are in fluid communication with each other.

In some embodiments, at least one of the balloons is bellowed.

In some embodiments, the transducer elements are on respective first faces of the flaps, and the balloons are coupled to respective second faces of the flaps that are opposite the first faces.

In some embodiments, the balloons are configured to at least partly cover edges of the flaps, when the balloons are inflated.

In some embodiments, the balloons are configured to at least partly cover the ultrasound transducer elements, when the balloons are inflated.

There is further provided, in accordance with some embodiments of the present invention, a method. The method includes inserting a catheter into an intra body space, passing a plurality of flaps from the catheter, the plurality of flaps being folded over each other in a folded configuration, and unfolding the flaps from the folded configuration, by inflating one or more balloons coupled to the flaps.

In some embodiments, the intra body space is a chamber of a heart.

In some embodiments, each one of the flaps includes one or more ultrasound transducer elements, and the method further includes using the ultrasound transducer elements to acquire an ultrasound image of the intra body space.

In some embodiments, inflating the balloons includes inflating the balloons with a saline solution.

In some embodiments, the method further includes folding the flaps back into the folded configuration, by deflating the balloons.

There is further provided, in accordance with some embodiments of the present invention, apparatus that includes a catheter, and a plurality of flaps configured to fold over each other in a folded configuration, and to fit inside the catheter while in the folded configuration. The apparatus further includes one or more balloons coupled to the flaps, the balloons being configured to, upon being inflated, unfold the flaps from the folded configuration.

The present invention will be more fully understood from the following detailed description of embodiments thereof, taken together with the drawings, in which:

DETAILED DESCRIPTION OF EMBODIMENTS

Overview

For certain ICE applications, a foldable ultrasound transducer assembly may be used. Such a transducer assembly may comprise, for example, a plurality of flaps, each of the flaps comprising a capacitive micro machined ultrasound transducer (CMUT) array or a piezoelectric micro machined ultrasound transducer (PMUT) array. Prior to deployment, the flaps are folded and contained within the delivery catheter. Upon the distal end of the delivery catheter reaching the area of interest within the heart, the transducer assembly is deployed from the catheter, the flaps are unfolded, and the ultrasound arrays are subsequently used to acquire ultrasound images of the intra cardiac space. Such foldable transducer assemblies allow for acquiring high-quality ultrasound images, without needing to pass an overly-large catheter through the vasculature of the subject.

Embodiments described herein relate to a balloon-based folding mechanism that may be used for a foldable ultrasound transducer assembly, or for any other foldable device deployed, for example, from a catheter. As described in detail below, embodiments described herein comprise one or more balloons coupled to the flaps. Upon being inflated, the balloons unfold the flaps; conversely, upon being deflated, the balloons fold the flaps.

The balloon-based folding mechanism described herein has certain advantages over other possible types of folding mechanisms, such as folding mechanisms that are primarily based on wires and/or springs. For example, the mechanism described herein is generally simpler to manufacture and operate than other mechanisms, and may alternatively or additionally be more efficient in power consumption. Moreover, the mechanism described herein may be safer than other types of mechanisms, at least in that (i) the balloons may provide protective cushioning that mitigates the effect of impact with the intra cardiac tissue, (ii) the balloons provide a smooth exterior surface at which blood clots are unlikely to form, and/or (iii) the balloons are biocompatible.

Apparatus Description

Figure 1:
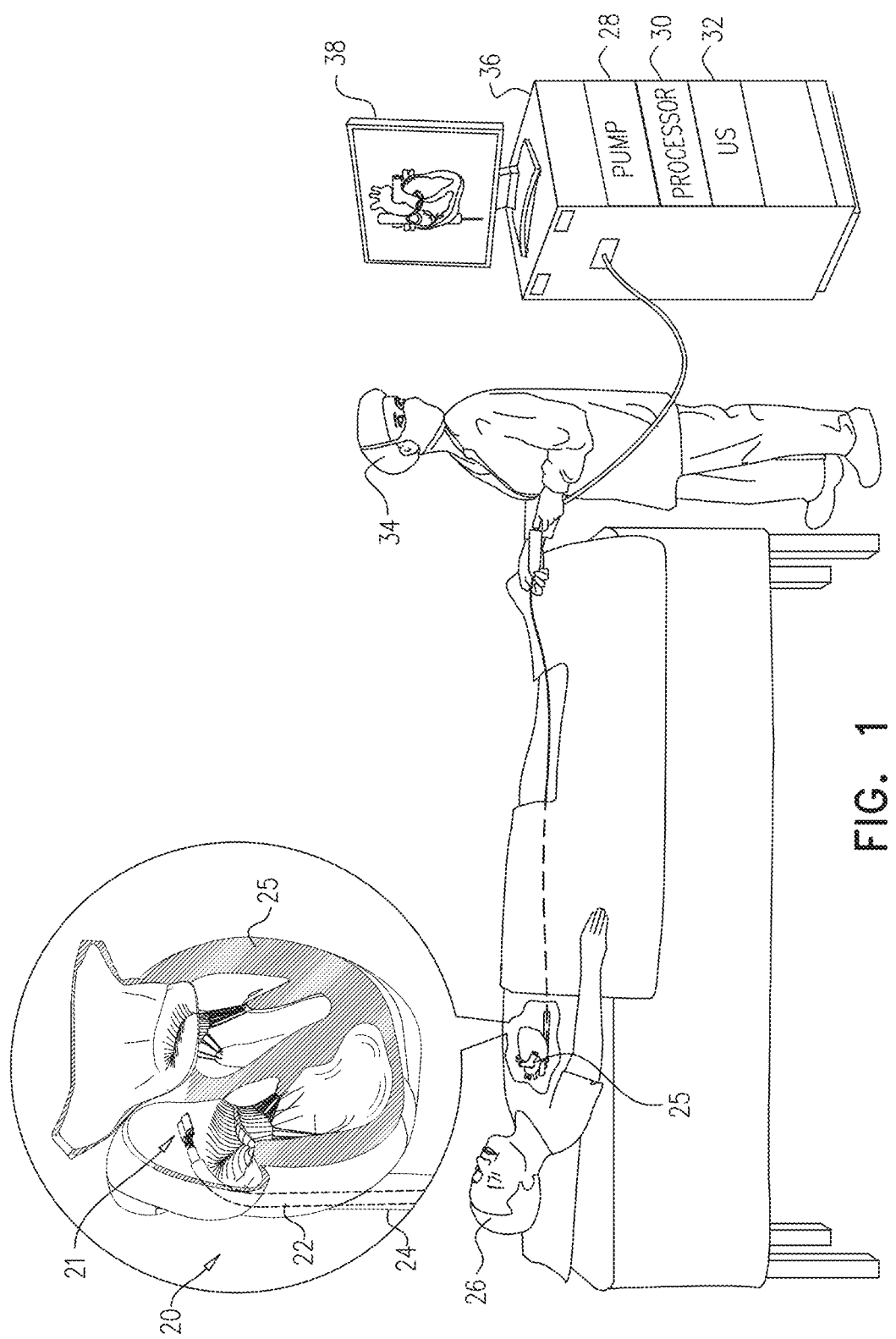
FIG. 1 is a schematic illustration of an ICE procedure using ICE apparatus, in accordance with some embodiments of the present invention.

Reference is initially made to FIG. 1, which is a schematic illustration of an ICE procedure using ICE apparatus 20, in accordance with some embodiments of the present invention. ICE apparatus 20 comprises a catheter 22, along with a foldable ultrasound transducer assembly 21 that is deployable from the distal end of catheter 22. As shown in the figure, during an ICE procedure, catheter 22 is inserted into the heart 25 of a subject 26, e.g., via an inferior vena cava 24 of subject 26. The distal end of the catheter is then navigated to the area of interest within the heart, such as a chamber of interest (e.g., the right atrium). Subsequently, transducer assembly 21 is deployed, and is used to acquire ultrasound images of the area of interest.

As shown in the figure, catheter 22 may be connected at its proximal end to a console 36. Console 36 may comprise, for example, an ultrasound (US) waveform generator 32, which generates the electrical signals that are converted, by the transducer assembly, to ultrasound waves. Console 36 may further comprise a pump 28, which pumps a fluid, such as a saline solution, to the distal end of the catheter, e.g., such as to inflate the balloons that are used to unfold the transducer assembly into its deployed configuration (as described in detail below). Console 36 may further comprise a processor 30 for processing signals received from the ultrasound transducer assembly, and/or for performing any other relevant functions. During the procedure, images acquired by the ultrasound transducer assembly may be displayed on a monitor 38, for viewing by the physician 34 who is conducting the procedure.

Although FIG. 1 relates specifically to an intra cardiac application, it is noted that apparatus and methods described herein may also be applied to other suitable applications. That is, catheter 22 may be inserted into any suitable intra body space, and transducer assembly 21 may be deployed and used within the intra body space, as described herein. Moreover, although the present description and figures relate mainly to ultrasound applications, it is noted that apparatus and methods described herein may be applied to any suitable application in which a folded tool is delivered (e.g., via a catheter) to a particular location (e.g., an intra body space), and then unfolded at the particular location.

Reference is now made to FIGS. 2A-D, which are schematic illustrations of foldable ultrasound transducer assembly 21, in accordance with some embodiments of the present invention.

Figure 2A:
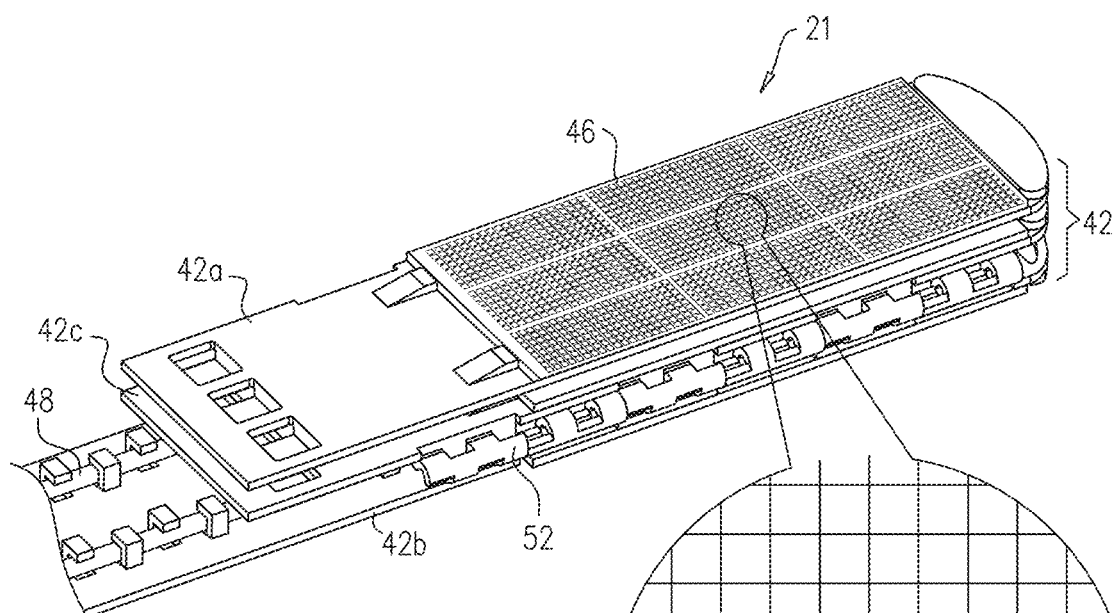
FIGS. 2A-D are schematic illustrations of a foldable ultrasound transducer assembly, in accordance with some embodiments of the present invention.

FIG. 2A shows transducer assembly 21 in a folded configuration. As shown in the figure, transducer assembly 21 comprises a plurality of flaps 42, which, in the folded configuration, fold over each other, such that the transducer assembly fits inside the catheter (FIG. 1). Each one of the flaps comprises one or more ultrasound transducer elements 50. For example, each one of the flaps may comprise an array 46 of capacitive or piezoelectric transducer elements 50. The ultrasound transducer elements are used to acquire an ultrasound image of the intra body space in which the transducer assembly is deployed.

In general, the transducer assembly may comprise any suitable number of flaps, such as two flaps, three flaps, or more than three flaps. For example, in the particular embodiment shown, the transducer assembly comprises three flaps 42a, 42b, and 42c.

Figure 2B:
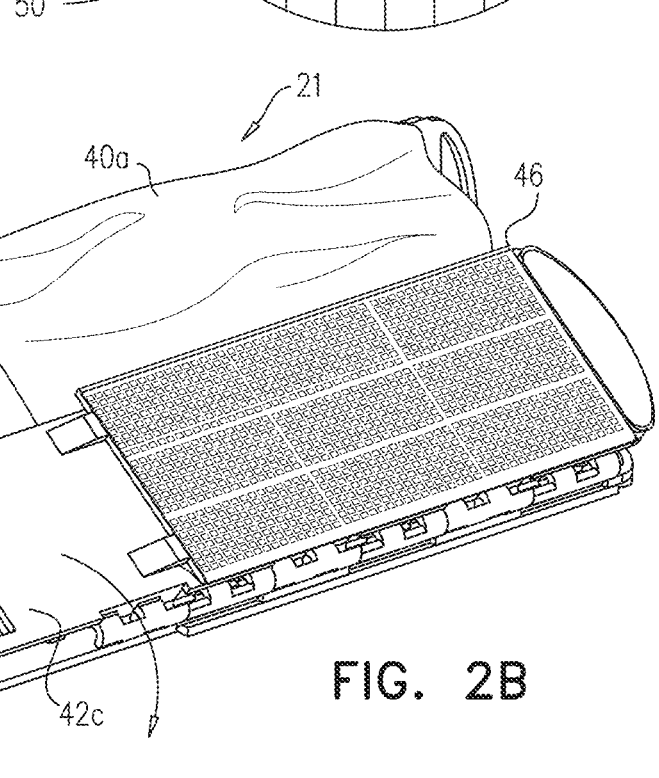
Figure 2C:
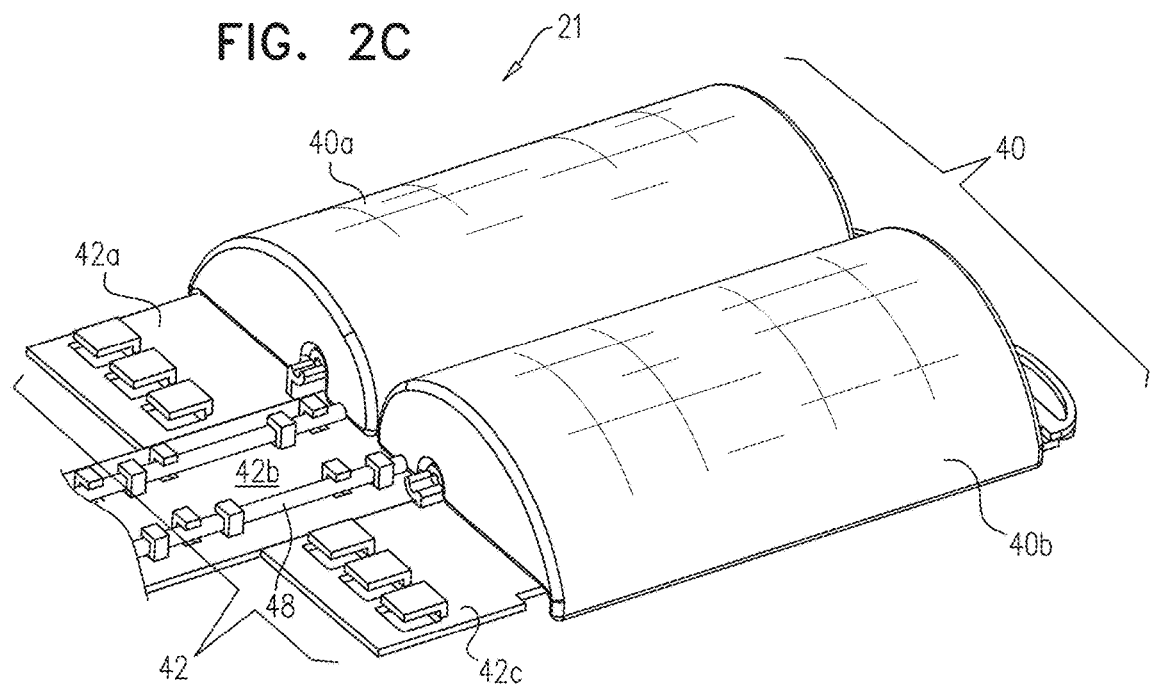
Figure 2D:
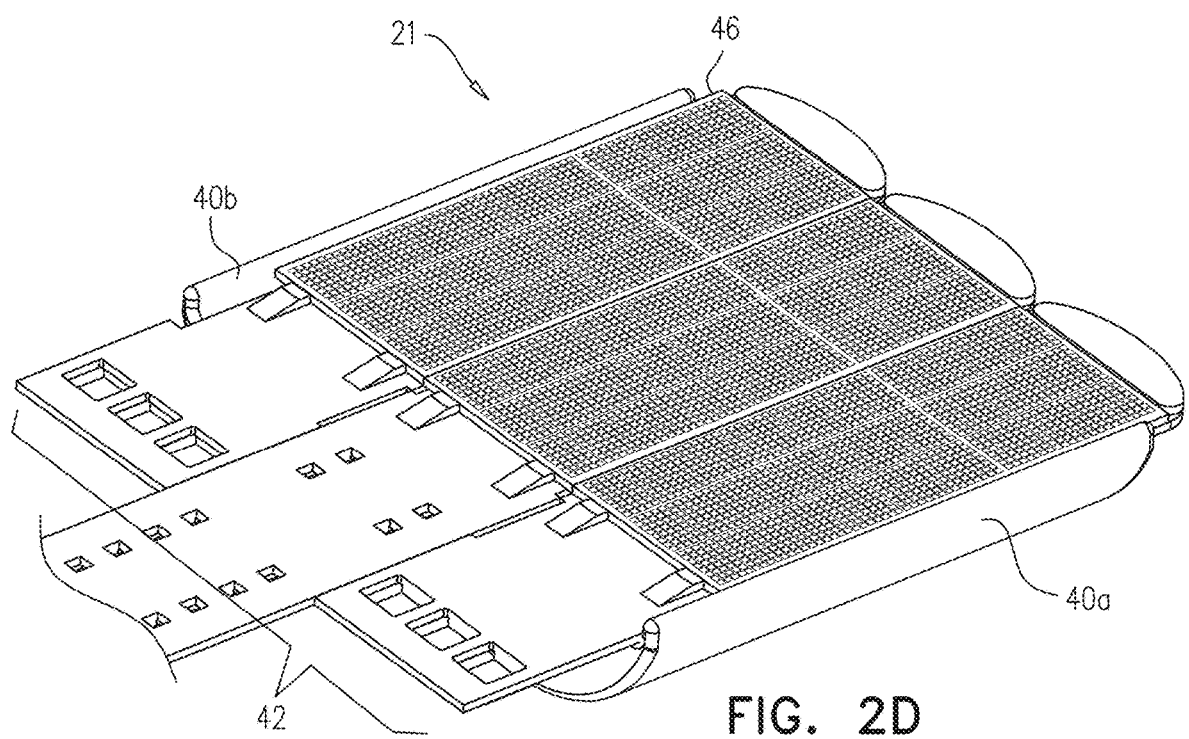

Upon deployment from the catheter, the flaps are unfolded, such that the transducer assembly first adopts the partially-unfolded configuration of FIG. 2B, and then adopts the fully-unfolded configuration of FIG. 2C-D. (FIGS. 2C-D show opposite faces of the transducer assembly in the fully-unfolded configuration.) Following the acquisition of one or more ultrasound images, the flaps are folded back into the folded configuration, the transducer assembly is reinserted into the catheter, and the catheter is withdrawn from the body of the subject.

As shows in FIG. 2B-D, the transducer assembly comprises one or more balloons 40 coupled to the flaps, which facilitate the folding and unfolding of the flaps. Typically, a respective subset of the balloons is coupled to each pair of adjacent flaps, i.e., a respective subset of the balloons "straddles" each pair of adjacent flaps. For example, FIG. 2C shows a first balloon 40a (which is a first subset of the balloons) coupled to both flaps 42a and 42b, and a second balloon 40b coupled to both flaps 42b and 42c. When the transducer assembly is in the folded configuration, the balloons are deflated, and generally do not occupy a significant amount of volume. (For example, the balloons may be "sandwiched" between the flaps.) As each balloon is inflated, the balloon pushes apart the two flaps to which it is coupled; thus, inflation of the balloons causes an unfolding of the flaps from the folded configuration. Conversely, as each balloon is deflated, the balloon pulls together the two flaps to which it is coupled; thus, deflation of the balloons causes a folding of the flaps back into the folded configuration.

Typically, each pair of adjacent flaps are hingedly coupled to one another (e.g., via one or more hinges 52, as shown), such that the flaps easily move between the folded and unfolded configurations.

It is noted that each subset of balloons may consist of any suitable number of balloons. For example, as an alternative to the single-balloon subsets shown in FIG. 2C, each subset may consist of a plurality of balloons arranged proximally-distally along a respective pair of adjacent flaps, as described below, for example, with reference to FIG. 3.

In general, balloons 40 may be manufactured from any suitable biocompatible material.

Typically, one or more fluid-delivery tubes 48, which run the length of the catheter from the proximal end of the catheter, deliver the fluid that is used to inflate the balloons. For example, fluid-delivery tubes 48 may deliver a saline solution from pump 28 (FIG. 1). An advantage of filling the balloons with saline is that no harm to the subject will result from the balloons being accidentally punctured while inside the subject.

In some embodiments, as shown, each of the balloons is inflated separately, via a separate fluid-delivery tube. In other embodiments, at least two of the balloons are inflated together, via a common fluid-delivery tube. For example, at least two of the balloons may be in fluid communication with one another, such that fluid is pumped by a single fluid-delivery tube into both of the balloons. Alternatively or additionally, a single fluid-delivery tube may bifurcate, at the distal end of the tube, into separate conduits, each of the conduits providing fluid to a respective one of the balloons.

In some embodiments, as shown, the balloons are not integrated with each other. In other embodiments, the balloons are integrated with each other. For example, at least two of the balloons may share a common wall, and/or may be in fluid communication with one another, as described above.

As shown in FIGS. 2C-D, in some embodiments, the balloons, upon being inflated, unfold the flaps from the folded configuration into a flat configuration. Alternatively, the balloons may unfold the flaps into any other suitable unfolded configuration.

In some embodiments, as shown in the figures, transducer elements 50 and balloons 40 are coupled to opposite faces of the flaps, i.e., each flap has transducer elements on one face, and one or more balloons coupled to the opposite face. In other embodiments, at least some balloons may be coupled to a face of a flap on which at some transducer elements are disposed. For example, as described below, a balloon may cover some of the transducer elements.

In some embodiments, the balloons, at least when inflated, at least partly cover the edges of the flaps. For example, FIGS. 2C-D show balloon 40a covering part of an edge of flap 42a, and balloon 40b covering part of an edge of flap 42c. The covering of the edges by the balloons provides for increased safety, in that (i) the balloons may provide protective cushioning that mitigates the effect of impact with the intra cardiac tissue, (ii) the balloons provide a smooth exterior surface at which blood clots are unlikely to form. Alternatively or additionally, the balloons, at least when inflated, may at least partly cover the ultrasound transducer elements. (In other words, the balloons may at least partly cover at least one of the ultrasound transducer elements.) As with the covering of the edges, the covering of the transducer elements may provide for increased safety.

Alternatively or additionally to balloons 40 partly covering the edges of the flaps and/or the transducer elements, additional balloons (not shown), situated over the edges of the flaps and/or the transducer elements, may be provided. Upon deployment of the transducer, these balloons may be inflated.

Figure 3:
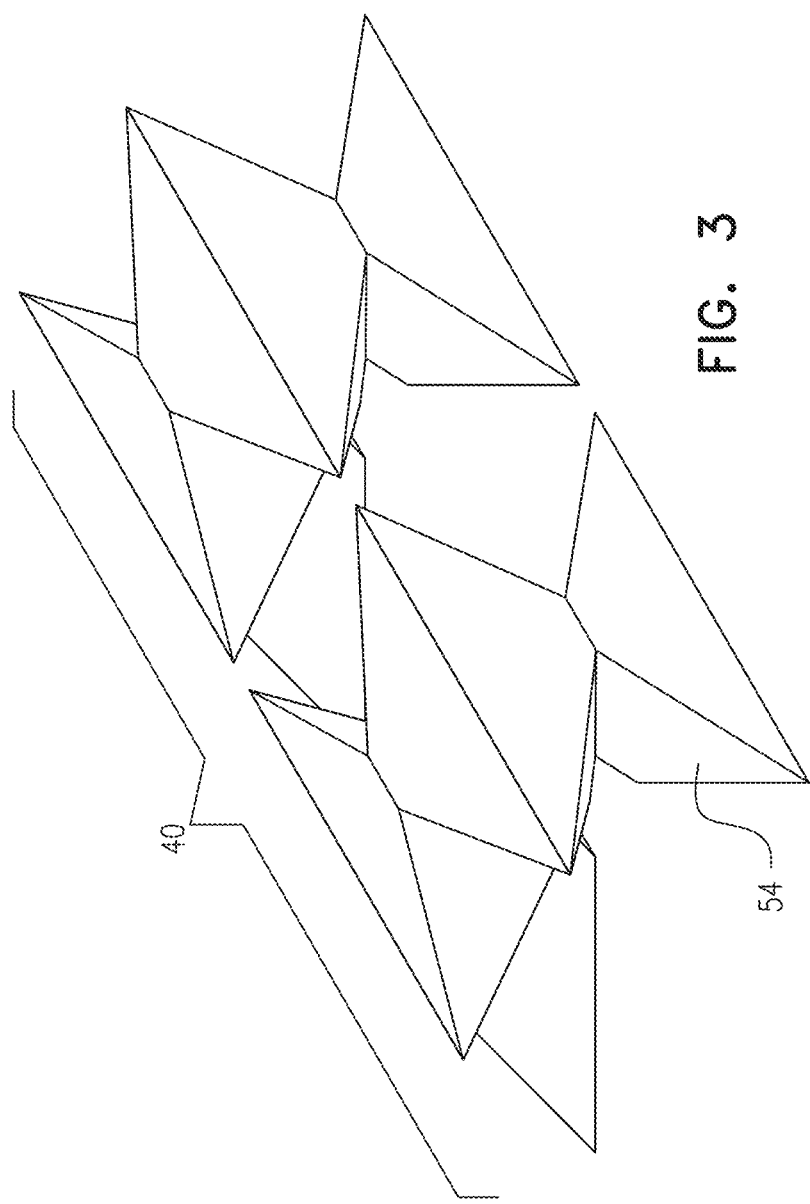
FIG. 3 is a schematic illustration of a plurality of inflated balloons, in accordance with some embodiments of the present invention.

Reference is now made to FIG. 3, which is a schematic illustration of a plurality of inflated balloons 40, in accordance with some embodiments of the present invention. The pair of balloons in FIG. 3 may take the place of one of the balloons shown in FIG. 2B, i.e., the pair of balloons in FIG. 3 may straddle a pair of adjacent flaps. Alternatively, one of the balloons in FIG. 3 may straddle one adjacent pair of flaps, and the other balloon may straddle the other adjacent pair of flaps.

While FIG. 2C shows an embodiment in which each of the balloons is half-cylindrical in shape, and has a single compartment, FIG. 3 shows two bellowed ("accordion-shaped") balloons, each of the bellowed balloons comprising an inflatable and collapsible array of compartments 54 that are in fluid communication with each other. Such a form may provide for a more compact folded configuration of the transducer assembly. (In general, it is noted that each of the balloons used for unfolding the flaps may have, when inflated, any suitable shape, and may comprise any suitable number of compartments in fluid communication with each other.)

It will be appreciated by persons skilled in the art that the present invention is not limited to what has been particularly shown and described hereinabove. Rather, the scope of embodiments of the present invention includes both combinations and sub combinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus comprising:
   a catheter;
   a plurality of flaps configured to fold over each other in a folded configuration or to unfold from each other in an unfolded configuration, each one of the flaps comprising one or more ultrasound transducer elements;
   two or more balloons coupled to the flaps, the two or more balloons being configured to unfold the flaps from the folded configuration into an unfolded configuration, and being further configured to fold the flaps from the unfolded configuration into a flat configuration; and
   one or more fluid-delivery tubes within the catheter that are fluidly connected to a source of fluid and to the two or more balloons, a pump for delivering fluid to at least one of the two or more balloons for unfolding the at least one of the flaps,
   wherein each balloon of the two or more balloons is coupled to two of the flaps.

2. The apparatus according to claim 1, wherein the plurality of flaps are configured to fit inside the catheter while in the folded configuration.

3. The apparatus according to claim 1, wherein the flaps comprise at least three flaps.

4. The apparatus according to claim 1, wherein at least one of the two or more balloons comprise a plurality of compartments that are in fluid communication with each other.

5. The apparatus according to claim 1, wherein at least one of the two or more balloons is bellowed.

6. The apparatus according to claim 1, wherein the transducer elements are on respective first faces of the flaps, and wherein the two or more balloons are coupled to respective second faces of the flaps that are opposite the first faces.

7. The apparatus according to claim 1, wherein the two or more balloons are configured to at least partly cover the ultrasound elements upon being inflated.

8. The apparatus according to claim 1, wherein the flaps comprise distal edges and lateral edges and wherein one of the two or more balloons upon being inflated, at least partly cover the lateral edges of the flaps.

9. The apparatus according to claim 1, wherein the two or more balloons are configured to be independently inflated and upon being inflated to unfold the flaps.

10. A method, comprising:
    inserting a catheter into an intrabody space;
    passing two or more flaps each one of the flaps comprising one or more ultrasound transducer elements from the catheter, the flaps being folded over each other in a folded configuration;
    unfolding the flaps from the folded configuration, by inflating two or more balloons coupled to the flaps; and
    folding the flaps back into the folded configuration, by deflating the two or more balloons, wherein one or more fluid-delivery tubes, which run the length of the catheter from a proximal end of the catheter, deliver fluid used to inflate the two or more balloons, wherein, when the apparatus is in the folded configuration, the two or more balloons are sandwiched between the flaps, wherein each balloon of the two or more balloons is coupled to two of the flaps, and wherein, as each balloon of the two or more balloons is deflated, the deflated balloon pulls together the two flaps to which it is coupled.

11. The method according to claim 10, wherein the intrabody space is a chamber of a heart.

12. The method according to claim 10, wherein the method further comprises using the ultrasound transducer elements to acquire an ultrasound image of the intrabody space.

13. The method according to claim 10, wherein unfolding the flaps from the folded configuration comprises unfolding the flaps into a flat configuration.

14. The method according to claim 10, wherein inflating the two or more balloons comprises inflating the two or more balloons with a saline solution.

15. The method according to claim 10, wherein the two or more balloons are configured to at least partly cover the ultrasonic transducer elements upon the balloons being inflated.

16. The method according to claim 10, wherein the flaps comprise distal edges and lateral edges and wherein the two or more balloons are configured to at least partly cover the lateral edges of the flaps upon being inflated.

17. The method according to claim 10, wherein the two or more balloons are configured to be independently inflated and upon being inflated to unfold the flaps.

* * * * *